(12) United States Patent
McEvaddy et al.

(10) Patent No.: US 11,406,799 B2
(45) Date of Patent: Aug. 9, 2022

(54) POUCH FORMING CATHETER

(71) Applicant: BOSTON SCIENTIFIC LIMITED, Hamilton (BM)

(72) Inventors: Matthew McEvaddy, County Galway (IE); Martin Lawrence Fawdry, County Galway (IE); Gary Duffy, County Kildare (IE); Eamonn J. Tuohy, County Tipperary (IE); Aiden Flanagan, County Galway (IE)

(73) Assignee: Boston Scientific Limited

( * ) Notice: Subject to any disclaimer, the term of this patent is extended or adjusted under 35 U.S.C. 154(b) by 541 days.

(21) Appl. No.: 16/361,192

(22) Filed: Mar. 21, 2019

(65) Prior Publication Data
US 2019/0217064 A1 Jul. 18, 2019

Related U.S. Application Data (63) Continuation of application No. PCT/US2017/054142, filed on Sep. 28, 2017.
(Continued)

(51) Int. Cl.
*A61M 25/10* (2013.01)
*A61F 2/00* (2006.01)
*A61B 17/32* (2006.01)

(52) U.S. Cl.
CPC ....... *A61M 25/1002* (2013.01); *A61F 2/0063* (2013.01); *A61B 2017/320048* (2013.01);
(Continued)

(58) Field of Classification Search
CPC ...... A61M 25/1002; A61M 2025/1072; A61M 2210/1021; A61B 2017/320048; A61F 2/0063
See application file for complete search history.

(56) References Cited

U.S. PATENT DOCUMENTS 2,849,002 A 8/1985 Oddo
5,425,357 A 6/1995 Moll
(Continued)

FOREIGN PATENT DOCUMENTS

| WO | 9107927 A1 | 6/1991 |
| WO | 2008065653 A1 | 6/2008 |
| WO | 2018064402 A1 | 4/2018 |

OTHER PUBLICATIONS

International Search Report and Written Opinion dated Dec. 19, 2017 for International Application No. PCT/US2017/054142.
(Continued)

*Primary Examiner* — Diane D Yabut
*Assistant Examiner* — Christina C Lauer
(74) *Attorney, Agent, or Firm* — Seager, Tufte & Wickhem, LLP (57) ABSTRACT

A dissection device may include an inflatable balloon disposed at a distal end of a catheter, the catheter having an inflation lumen extending through the catheter to an interior space defined within the inflatable balloon. The inflatable balloon may include a top wall, a bottom wall spaced apart from the top wall, an outer perimeter wall extending between the top wall and the bottom wall, and a plurality of inner walls each extending between the top wall and the bottom wall and in sealing contact with the outer perimeter wall at a first end of the inner wall. The inflatable balloon may include a series of interconnected chambers including a central chamber in direct fluid communication with the inflation lumen, and laterally disposed chambers each having an opening fluidly connecting to each adjacent chamber.

18 Claims, 9 Drawing Sheets

Related U.S. Application Data (60) Provisional application No. 62/402,393, filed on Sep. 30, 2016.

(52) U.S. Cl.
CPC .................. *A61F 2002/0072* (2013.01); *A61F 2250/0059* (2013.01); *A61M 2025/1072* (2013.01); *A61M 2025/1081* (2013.01); *A61M 2210/1021* (2013.01)

(56) References Cited

U.S. PATENT DOCUMENTS

| | | | |
|---|---|---|---|
| 5,514,153 A | 5/1996 | Bonutti | |
| 5,540,711 A | 7/1996 | Kieturakis et al. | |
| 5,575,759 A | 11/1996 | Moll et al. | |
| 5,607,443 A | 3/1997 | Kieturakis et al. | |
| 5,667,520 A | 9/1997 | Bonutti | |
| 5,720,762 A | 2/1998 | Bass | |
| 5,728,119 A | 3/1998 | Smith et al. | |
| 5,730,756 A | 3/1998 | Kieturakis et al. | |
| 5,746,762 A | 5/1998 | Bass | |
| 5,772,680 A | 6/1998 | Kieturakis et al. | |
| 5,776,159 A | 7/1998 | Young | |
| 5,779,728 A | 7/1998 | Lunsford et al. | |
| 5,817,123 A | 10/1998 | Kieturakis et al. | |
| 5,827,318 A | 10/1998 | Bonutti | |
| 5,855,588 A | 1/1999 | Young | |
| 5,865,728 A | 2/1999 | Moll et al. | |
| 5,871,497 A | 2/1999 | Young | |
| 5,925,058 A | 7/1999 | Smith et al. | |
| 5,984,943 A | 11/1999 | Young | |
| 6,004,337 A | 12/1999 | Kieturakis et al. | |
| 6,042,596 A | 3/2000 | Bonutti | |
| 6,066,154 A * | 5/2000 | Reiley | A61B 17/7275 606/94 |
| 6,264,604 B1 | 7/2001 | Kieturakis et al. | |
| 6,277,136 B1 | 8/2001 | Bonutti | |
| 6,358,266 B1 | 3/2002 | Bonutti | |
| 6,364,892 B1 | 4/2002 | Jervis | |
| 6,432,121 B1 | 8/2002 | Jervis | |
| 6,436,118 B1 | 8/2002 | Kayan | |
| 6,540,764 B1 | 4/2003 | Kieturakis et al. | |
| 6,632,234 B2 | 10/2003 | Kieturakis et al. | |
| 6,866,676 B2 | 3/2005 | Kieturakis et al. | |
| 7,001,405 B2 | 2/2006 | Kieturakis et al. | |
| 7,179,272 B2 | 2/2007 | Kieturakis et al. | |
| 7,641,688 B2 | 1/2010 | Lesh | |
| 7,744,617 B2 | 6/2010 | Lunsford et al. | |
| 7,918,870 B2 | 4/2011 | Kugler et al. | |
| 7,938,819 B2 | 5/2011 | Kugler et al. | |
| 7,998,201 B2 | 8/2011 | Lesh | |
| 7,998,202 B2 | 8/2011 | Lesh | |
| 8,025,655 B2 | 9/2011 | Kugler et al. | |
| 8,083,727 B2 | 12/2011 | Kugler et al. | |
| 8,152,310 B2 | 4/2012 | DeCusatis et al. | |
| 8,157,831 B2 | 4/2012 | Kieturakis et al. | |
| 8,202,246 B2 | 6/2012 | Kugler et al. | |
| 8,282,665 B2 | 10/2012 | Kieturakis et al. | |
| 8,323,261 B2 | 12/2012 | Kugler et al. | |
| 8,328,839 B2 | 12/2012 | Criscuolo | |
| 8,961,494 B2 | 2/2015 | Kugler et al. | |
| 9,308,019 B2 | 4/2016 | Kugler et al. | |
| 2001/0029388 A1 | 10/2001 | Kieturakis et al. | |
| 2002/0095160 A1 | 7/2002 | Bonutti | |
| 2003/0191490 A1 | 10/2003 | Kieturakis et al. | |
| 2003/0236544 A1 | 12/2003 | Lunsford et al. | |
| 2004/0015182 A1 | 1/2004 | Kieturakis et al. | |
| 2004/0167557 A1 | 8/2004 | Kieturakis et al. | |
| 2006/0173483 A1 | 8/2006 | Kieturakis et al. | |
| 2007/0093779 A1 | 4/2007 | Kugler et al. | |
| 2007/0093780 A1 | 4/2007 | Kugler et al. | |
| 2007/0118170 A1 | 5/2007 | Kieturakis et al. | |
| 2007/0162067 A1 | 7/2007 | Lunsford et al. | |
| 2008/0058854 A1 | 3/2008 | Kieturakis et al. | |
| 2008/0275569 A1 | 11/2008 | Lesh | |
| 2009/0024215 A1 | 1/2009 | Lesh | |
| 2009/0024226 A1 | 1/2009 | Lesh | |
| 2009/0024227 A1 | 1/2009 | Lesh | |
| 2009/0024228 A1 | 1/2009 | Lesh | |
| 2009/0048684 A1 | 2/2009 | Lesh | |
| 2009/0182368 A1 | 7/2009 | Lunsford et al. | |
| 2010/0063534 A1 | 3/2010 | Kugler et al. | |
| 2010/0069945 A1 | 3/2010 | Olson et al. | |
| 2010/0249946 A1 | 9/2010 | Lesh et al. | |
| 2011/0144742 A1 | 6/2011 | Madrid et al. | |
| 2011/0166579 A1 * | 7/2011 | Deem | A61F 2/30 606/90 |
| 2011/0276072 A1 | 11/2011 | Kugler et al. | |
| 2011/0276079 A1 | 11/2011 | Kugler et al. | |
| 2012/0136382 A1 | 5/2012 | Kugler et al. | |
| 2013/0103070 A1 | 4/2013 | Kugler et al. | |
| 2013/0110144 A1 | 5/2013 | Olson et al. | |
| 2013/0304108 A1 | 11/2013 | Weber et al. | |
| 2013/0310868 A1 | 11/2013 | Kugler et al. | |
| 2014/0128900 A1 | 5/2014 | Jacobs et al. | |
| 2014/0276790 A1 * | 9/2014 | Raybin | A61B 18/00 606/41 |
| 2014/0277068 A1 | 9/2014 | Kugler et al. | |
| 2015/0080928 A1 | 3/2015 | Kugler et al. | |
| 2015/0231373 A1 | 8/2015 | Kugler et al. | |
| 2016/0183953 A1 | 6/2016 | Kugler et al. | |
| 2017/0252544 A1 | 9/2017 | Gomes et al. | |

OTHER PUBLICATIONS

International Report On Patentability and Written Opinion dated Apr. 11, 2019 for International Application No. PCT/US2017/054142.

International Search Report and Written Opinion dated Dec. 3, 2019 for International Application No. PCT/US2019/048384.

* cited by examiner

POUCH FORMING CATHETER

CROSS-REFERENCE TO RELATED APPLICATIONS

This application is a continuation of International Application No. PCT/US2017/054142, filed Sep. 28, 2017, which claims the benefit of priority under 35 U.S.C. § 119 to U.S. Provisional Application No. 62/402,393, filed Sep. 30, 2016, the disclosures of which are incorporated herein by reference in their entirety.

TECHNICAL FIELD

The work leading to this invention has received funding from the European Union's Seventh Framework Programme (FP7/2007-2013) under grant agreement No. 267867, and from the Spanish R&D&I National Plan Program (2008-2011) under subprogram Juan de la Cierva, proposal JCI-2012-12517.

The present disclosure pertains to medical devices, and methods for manufacturing medical devices. More particularly, the present disclosure pertains to medical devices for forming a pouch between layers of tissue.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

In a first aspect, a dissection device may comprise an inflatable balloon disposed at a distal end of a catheter. The catheter may have an inflation lumen extending through the catheter to an interior space defined within the inflatable balloon. The inflatable balloon may comprise a top wall, a bottom wall spaced apart from the top wall, an outer perimeter wall extending between the top wall and the bottom wall, and a plurality of inner walls each extending between the top wall and the bottom wall and in sealing contact with the outer perimeter wall at a first end of the inner wall.

In addition or alternatively, and in a second aspect, each of the plurality of inner walls includes a second end opposite the first end, the second end being spaced apart from the outer perimeter wall.

In addition or alternatively, and in a third aspect, a relative position of the first end of each inner wall within the inflatable balloon and a relative position of the second end of each inner wall within the inflatable balloon are transposed on adjacent inner walls.

In addition or alternatively, and in a fourth aspect, a distance between two opposing points on the outer perimeter wall in a plane through a center of the inflatable balloon is greater than a distance from the top wall to the bottom wall measured perpendicular to the plane through the center of the inflatable balloon.

In addition or alternatively, and in a fifth aspect, the distance from the top wall to the bottom wall measured perpendicular to the plane through the center of the inflatable balloon decreases in a direction laterally outward from the center of the inflatable balloon within the plane.

In addition or alternatively, and in a sixth aspect, a central longitudinal axis of the catheter lies within the plane through the center of the inflatable balloon.

In addition or alternatively, and in a seventh aspect, the inflatable balloon comprises a plurality of internal chambers defined by the plurality of inner walls.

In addition or alternatively, and in an eighth aspect, the inflation lumen is fluidly connected directly to a central internal chamber of the plurality of internal chambers.

In addition or alternatively, and in a ninth aspect, inflation media introduced into the interior space through the inflation lumen fills the plurality of internal chambers sequentially from the central internal chamber outward.

In addition or alternatively, and in a tenth aspect, the central internal chamber includes a generally circular cross-section.

In addition or alternatively, and in an eleventh aspect, each internal chamber disposed laterally outward from the central internal chamber has an elliptical cross-section.

In addition or alternatively, and in a twelfth aspect, the elliptical cross-section has a major dimension greater than a diameter of the central internal chamber.

In addition or alternatively, and in a thirteenth aspect, the major dimension increases in each successively further outward internal chamber.

In addition or alternatively, and in a fourteenth aspect, each of the plurality of inner walls are oriented generally parallel to a central longitudinal axis of the catheter.

In addition or alternatively, and in a fifteenth aspect, a proximal end of the inflatable balloon includes a proximally tapered portion coupled to an outer surface of the catheter.

In addition or alternatively, and in a sixteenth aspect, a dissection device for forming a pouch in an abdominal wall may comprise a catheter having an inflation lumen extending therethrough, and a non-compliant inflatable balloon attached to a distal end of the catheter in fluid communication with the inflation lumen, the inflatable balloon being expandable from a collapsed delivery configuration to an expanded configuration having a generally flattened profile. The inflatable balloon may comprise a series of interconnected longitudinally-oriented chambers including a central chamber in direct fluid communication with the inflation lumen, and laterally disposed chambers each having an opening fluidly connecting to each adjacent chamber. The series of interconnected longitudinally-oriented chambers may be configured to inflate laterally outward from the central chamber.

In addition or alternatively, and in a seventeenth aspect, the inflatable balloon includes a proximally tapered portion coupled to an outer surface of the catheter.

In addition or alternatively, and in an eighteenth aspect, the opening fluidly connecting the central chamber to each immediately adjacent chamber is positioned proximate a first end of the inflatable balloon.

In addition or alternatively, and in a nineteenth aspect, each opening fluidly connecting the chambers immediately adjacent to the central chamber to an immediately adjacent, laterally outwardly disposed chamber is positioned proximate a second opposing end of the inflatable balloon.

In addition or alternatively, and in a twentieth aspect, a method of forming a pouch within an abdominal wall may comprise:

inserting a dissection device between a first layer of tissue of the abdominal wall and a second layer of tissue of the abdominal wall immediately adjacent the first layer of tissue, the dissection device including an inflatable balloon disposed at a distal end of a catheter, the inflatable balloon comprising a top wall, a bottom wall spaced apart from the top wall, an outer perimeter wall extending between the top wall and the bottom wall, and a plurality of inner walls each extending between the top wall and the bottom wall and in sealing contact with the outer perimeter wall at a first end of the inner wall;

positioning the dissection device at a desired location of the pouch within the abdominal wall;

inflating the inflatable balloon within the abdominal wall, thereby separating the first layer of tissue from the second layer of tissue to form the pouch within the abdominal wall;

deflating the inflatable balloon within the abdominal wall; and withdrawing the dissection device from the abdominal wall.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description of various embodiments in connection with the accompanying drawings, in which.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention.

Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some diseases may negatively affect the quality of life of various people all over the world. Some diseases may be chronic, lifelong illnesses requiring constant treatment and/or intervention. For example, diabetes results from the pancreas not producing enough insulin or the cells of the body not properly responding to the insulin produced. Some diabetes patients require insulin injections or other medications to manage their condition and/or to reduce complications. Promising new or alternative therapies continue to be developed. Disclosed herein are minimally-invasive devices for forming a pouch in an abdominal wall to allow insertion and/or implantation of a diabetes-reversing implant or similar device in an area that is relatively easily accessed surgically and is highly vascularized.

Figure 1:
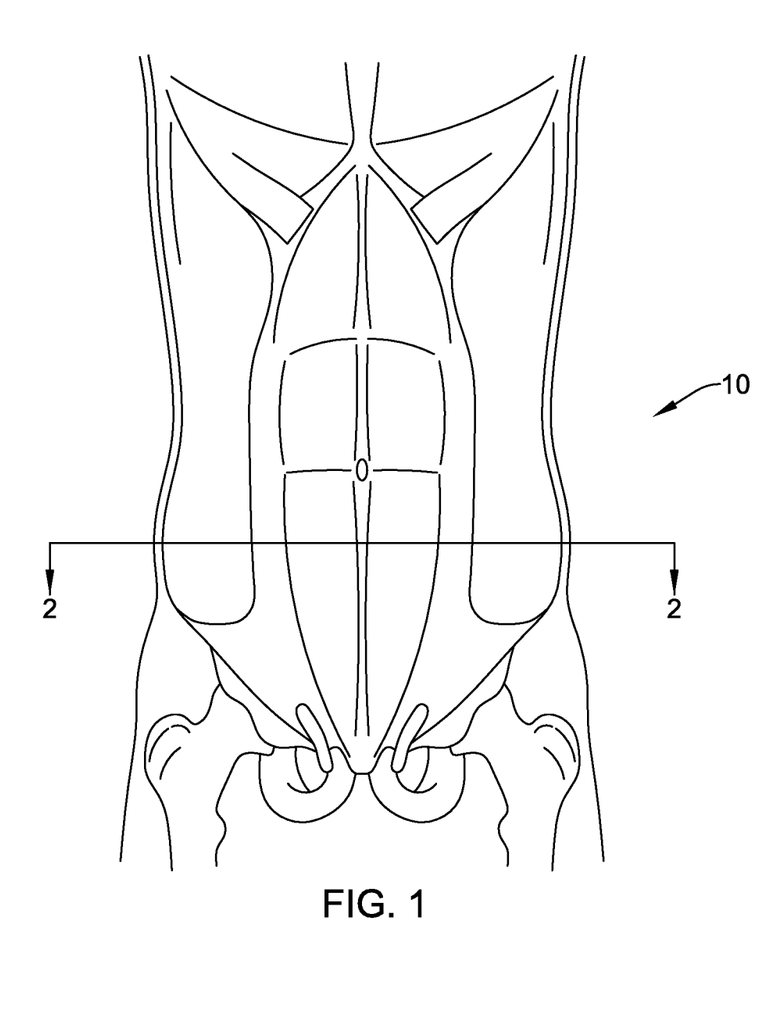
FIG. 1 is a partial anterior cut-away view of an abdomen of a human body.

FIG. 1 illustrates a partial cut-away anterior view of the abdominal area 10 of the human body. In some embodiments, an abdominal pouch may be formed on a left side of the body (e.g., laterally to the left of the midsagittal plane). Other locations may also be suitable for various procedures and/or alternatives, and use of the disclosed devices is not limited to the left anterior portion of the body.

Figure 2:
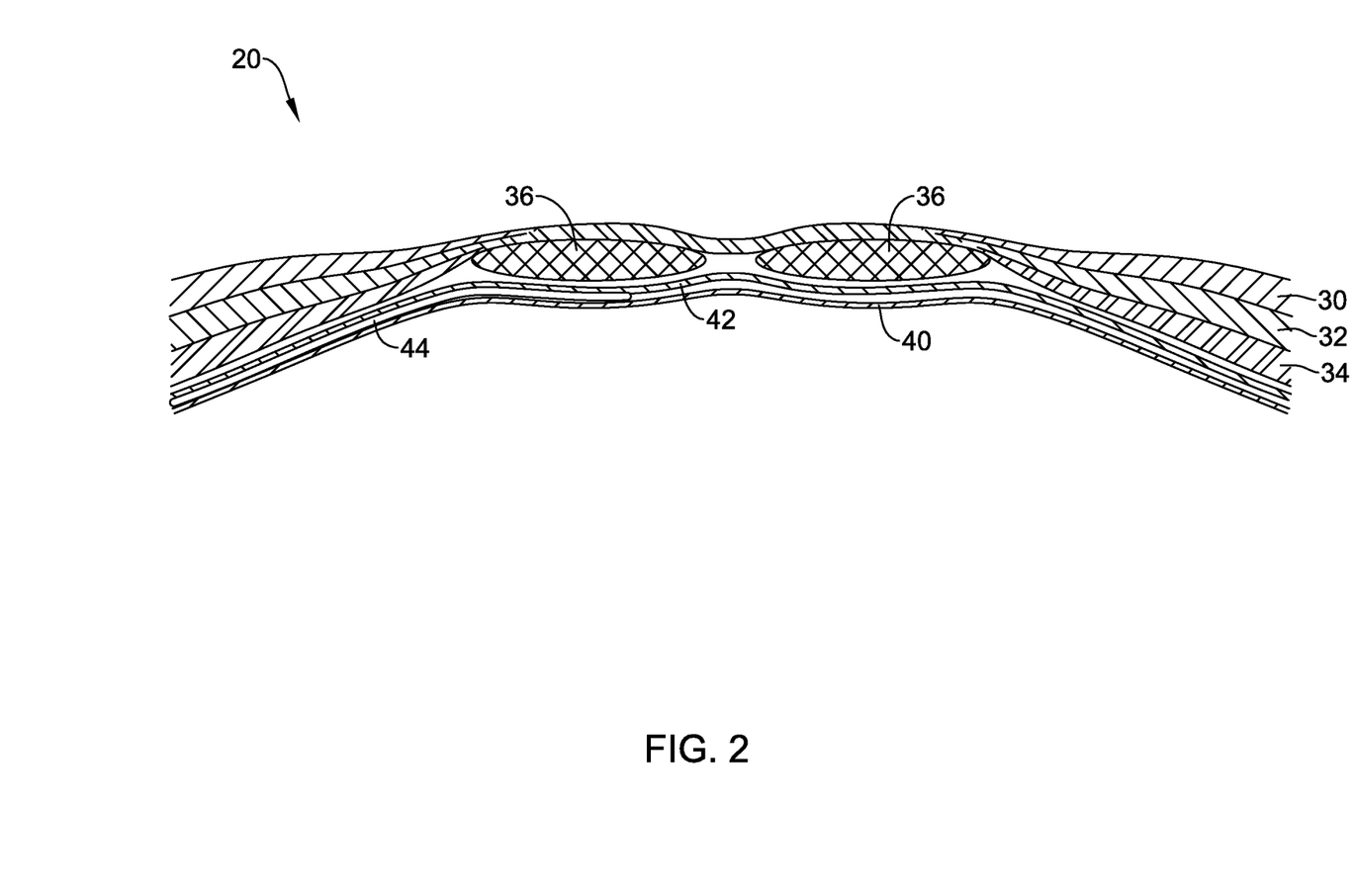
FIG. 2 is a partial cross-sectional view of an anterior wall of an abdomen of a human body.

FIG. 2 illustrates a partial cross-section of an anterior abdominal wall 20 of the abdominal area 10 of the human body. Some elements of the abdominal wall 20 may be seen in FIG. 2. The abdominal wall 20 includes three flat muscles situated laterally—the external oblique 30, the internal oblique 32, and the transversus abdominus 34. The abdominal wall 20 includes two vertical muscles situated near the mid-line of the body, the rectus abdominis 36 and the pyramidalis (not visible). In some embodiments, a dissection device may be used to form an abdominal pouch 44 between the tissue layers of the parietal peritoneum 40 and the transversalis fascia 42. This area of tissue layers lies beneath the abdominal muscles and on top of (e.g., anterior of) the intestines in the pubic and/or left groin areas of the abdomen.

Figure 3:
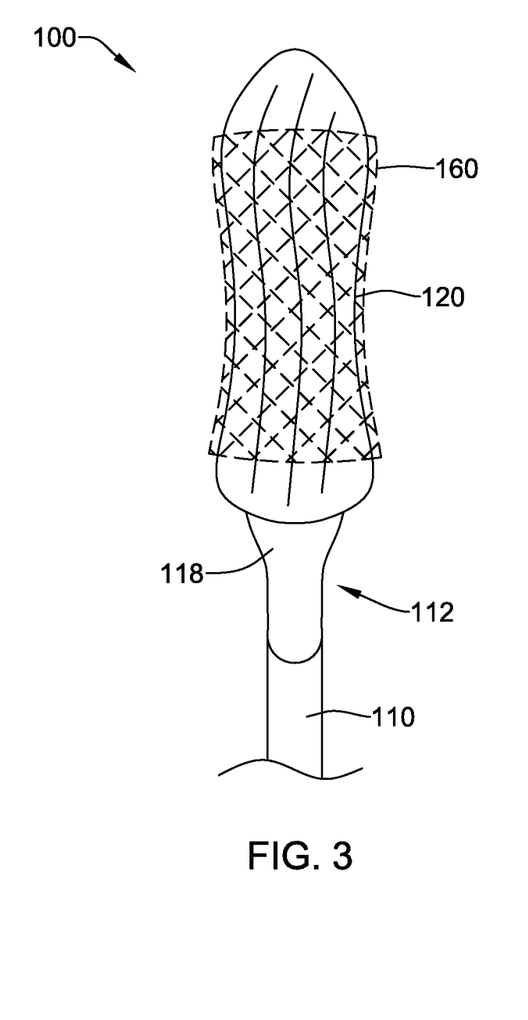
FIG. 3 illustrates an example dissection device in a collapsed delivery configuration.
Figure 4:
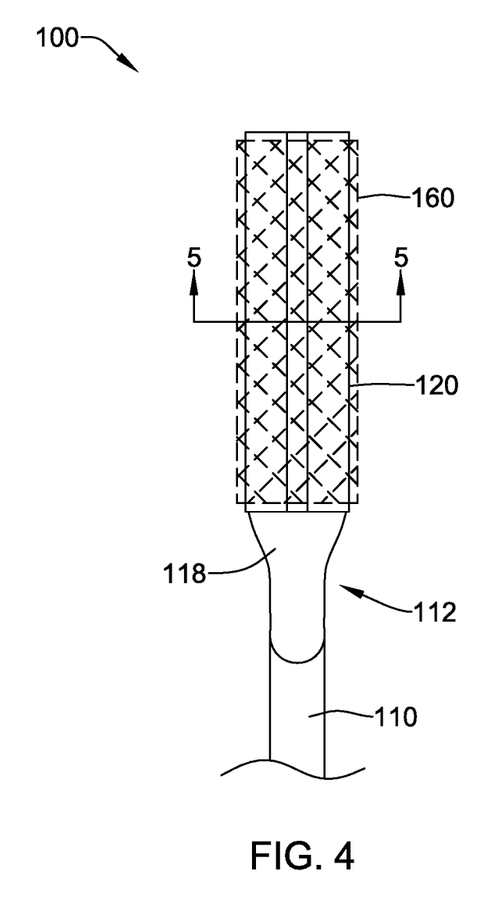
FIG. 4 illustrates an example dissection device in a collapsed delivery configuration.
Figure 5:
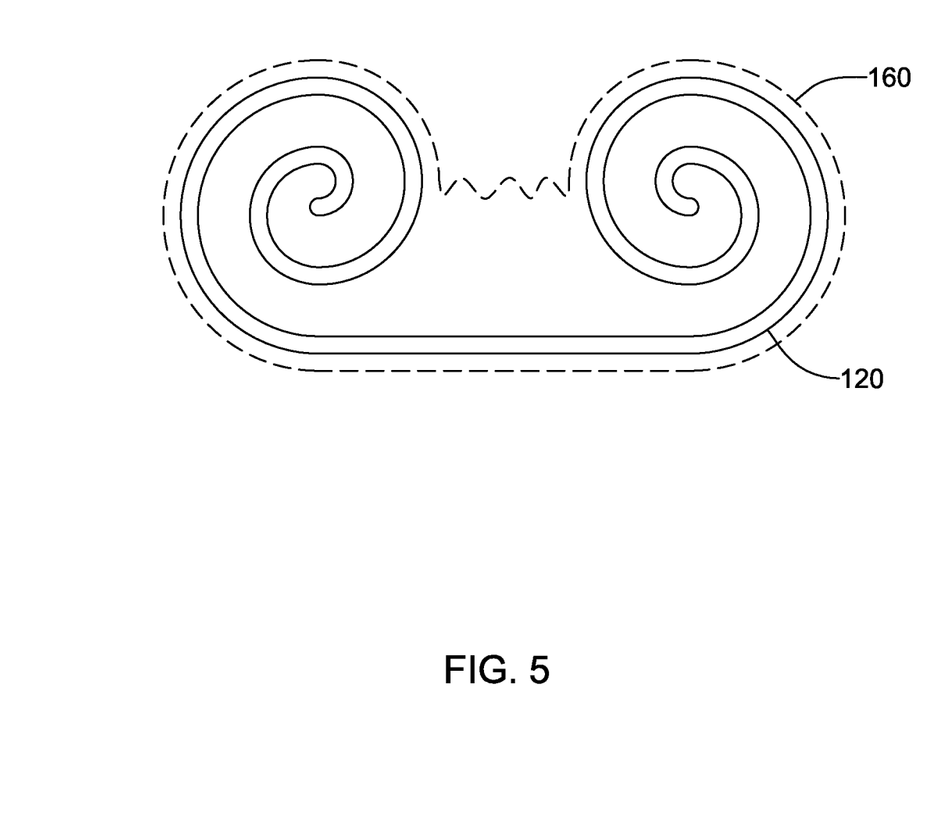
FIG. 5 is a cross-sectional view of the example dissection device of FIG. 4.
Figure 6:
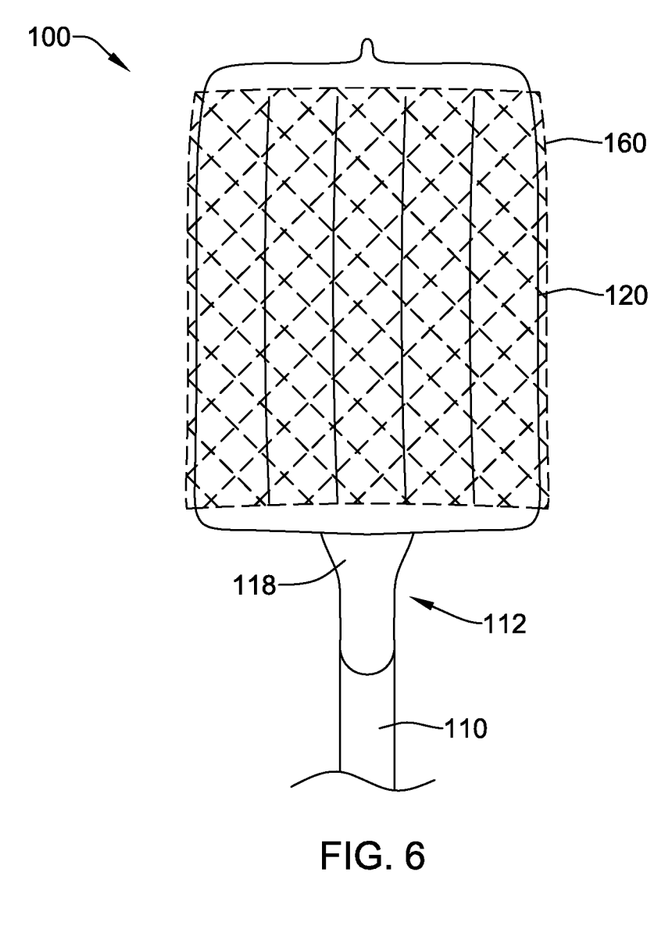
FIG. 6 illustrates an example dissection device in an expanded configuration.

An example dissection device 100 for forming an abdominal pouch may include an inflatable balloon 120 disposed at, coupled to, and/or attached to a distal end 112 of a catheter 110, as seen in FIGS. 3, 4, and 6. In some embodiments, a proximal end of the inflatable balloon 120 may include a proximally tapered portion 118 coupled to an outer surface of the catheter 110. In some embodiments, the proximally tapered portion 118 may be integrally formed with the inflatable balloon 120. In some embodiments, the proximally tapered portion 118 may include a conical element secured to the outer surface of the catheter 110 adjacent the proximal end of the inflatable balloon 120. In some embodiments, the proximally tapered portion 118 may aid in removal of the inflatable balloon 120 from a target site. In some embodiments, the inflatable balloon 120 may be a non-compliant polymeric balloon. In some embodiments, the inflatable balloon 120 may be a compliant polymeric balloon having some sort of support structure limiting how far the balloon may stretch and/or extend. Other suitable materials are also contemplated. The inflatable balloon 120 may be expandable from a collapsed delivery configuration, as seen in FIGS. 3, 4, and 5 for example, to an expanded configuration having a generally flattened profile, as seen in FIG. 6 for example. In the collapsed delivery configuration, the inflatable balloon 120 may be folded, wrapped, crimped, rolled, coiled, etc. to a smaller overall profile than the expanded configuration to facilitate delivery to and implantation at the target site—within the abdominal wall 20, for example. FIGS. 4 and 5 illustrate an example inflatable balloon 120 in a collapsed delivery configuration wherein lateral edges and/or sides of the inflatable balloon 120 are each rolled inwardly toward a center line of the inflatable balloon 120 and/or the catheter 110 in opposing directions. Some suitable but non-limiting materials for the inflatable balloon 120, for example polymeric materials, are described below.

In some embodiments, the dissection device 100 may optionally include an outer sleeve 160 loosely disposed about and/or at least partially surrounding the inflatable balloon 120. In some embodiments, at least a portion of the outer sleeve 160 may be bunched up and/or folded between portions of the inflatable balloon 120 in the collapsed delivery configuration (e.g., between folds, between rolled up portions, etc.), as seen in FIGS. 3, 4, and 5 for example. In some embodiments, the outer sleeve 160 may be formed from an elastic, resilient, and/or compliant material. In some embodiments, the outer sleeve 160 may be formed from an inelastic or non-resilient material. In some embodiments, the outer sleeve 160 may be an expandable material capable of stretching and/or expanding (e.g., a mesh, a net, a stent-like structure, etc.) from a collapsed delivery configuration to an expanded configuration along with the inflatable balloon 120, as seen in FIG. 6 for example. Some suitable but non-limiting materials for the outer sleeve 160, for example polymeric or metallic materials, are described below.

In use, the outer sleeve 160 may serve to reduce and/or minimize rubbing and/or friction between the inflatable balloon 120 and the tissue layers of the parietal peritoneum 40 and the transversalis fascia 42 when inflating the inflatable balloon 120 to form the abdominal pouch 44. After expanding the inflatable balloon 120 (and the outer sleeve 160) to the expanded configuration and forming the abdominal pouch 44, the inflatable balloon 120 may be deflated and the outer sleeve 160 left behind within the abdominal pouch in engagement with the tissue layers of the parietal peritoneum 40 and the transversalis fascia 42 (e.g., the walls of the abdominal pouch 44) to line the abdominal pouch 44 and help prevent re-adhesion between the tissue layers of the parietal peritoneum 40 and the transversalis fascia 42 until a medical implant or device is positioned in the abdominal pouch 44. In some embodiments, a period of time may pass between formation of the abdominal pouch 44 and implantation of the medical implant or device. Depending on how long the period of time is, the outer sleeve 160 may permit the tissue layers of the parietal peritoneum 40 and the transversalis fascia 42 to recover from inflammation caused by dissection with the inflatable balloon 120 and/or to minimize reaction to the eventual implanted medical implant or device.

In some embodiments, the outer sleeve 160 may include a coating and/or substance disposed on and/or eluting from the outer sleeve 160 which may include a vascular endothelial growth factor (VEGF) and/or other substance configured to stimulate the growth of new blood vessels such that a highly vascularized "bed" is created around the outer sleeve 160 and/or the abdominal pouch 44 to receive the implanted medical implant or device. Similarly, the inflatable balloon 120 may be coated with, inject, release, and/or otherwise deposit a substance (e.g., a gel, a solution, etc.) in the abdominal pouch 44 during and/or after inflation of the inflatable balloon 120 to the expanded configuration to reduce and/or minimize tissue damage and/or fibrosis, and/or to maintain patency of the abdominal pouch 44 for the delivery of the medical implant or device at some later point in time. In some embodiments, the substance may include and/or release pro-angiogenic elements to encourage development of the vascularized "bed" prior to implantation of the medical implant or device.

Figure 8:
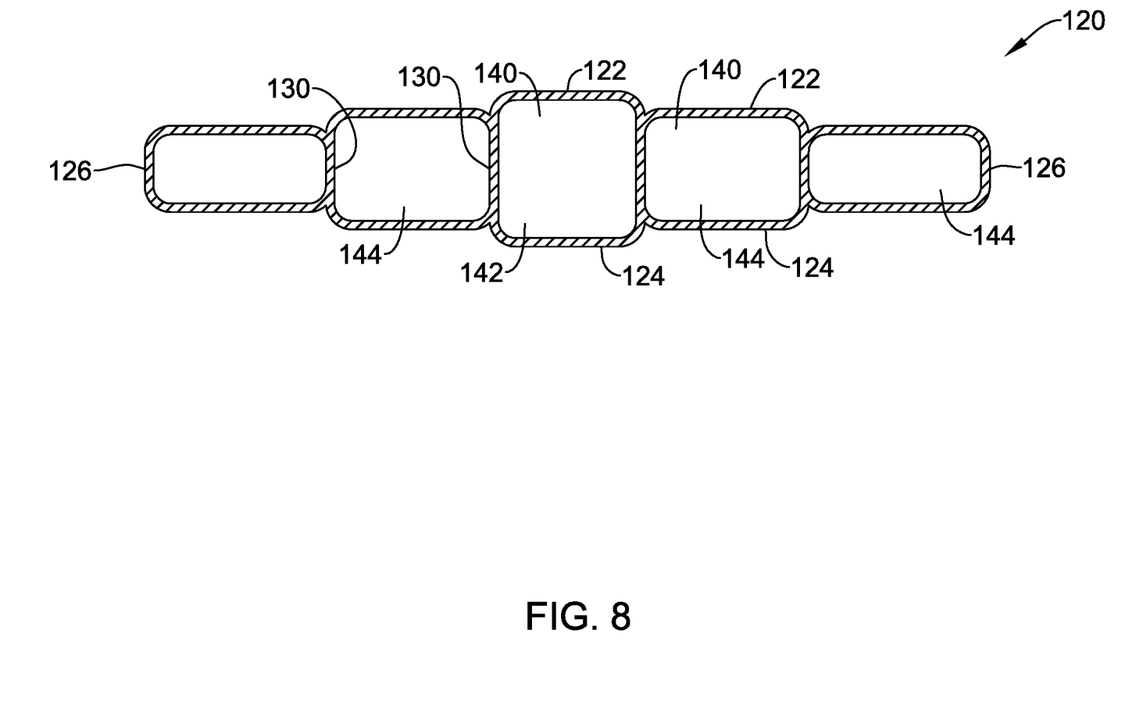
FIG. 8 is a cross-sectional view of an example dissection device.
Figure 9:
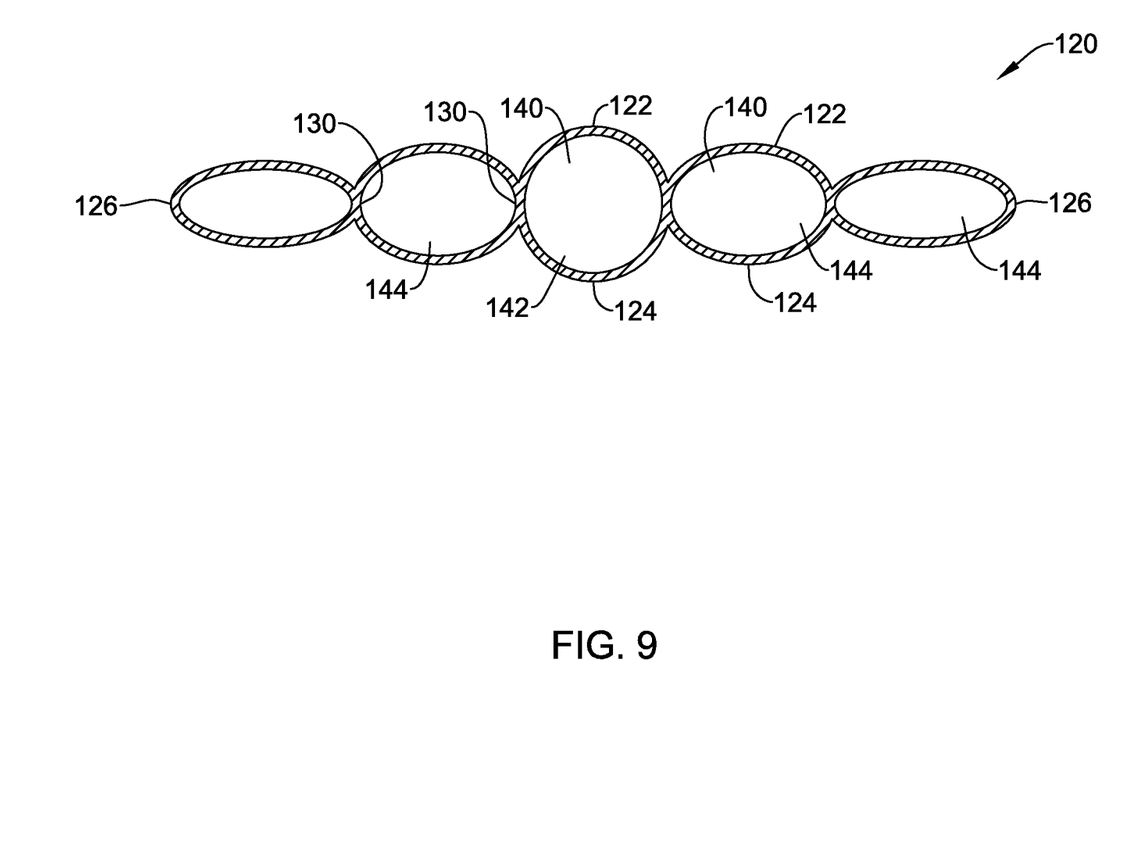
FIG. 9 is a cross-sectional view of an example dissection device.

As most easily seen in the cross-sectional views of FIGS. 8 and 9, the inflatable balloon 120 may comprise a top wall 122 and a bottom wall 124 spaced apart from the top wall 122. In some embodiments, the inflatable balloon 120 may comprise an outer perimeter wall 126 extending between the top wall 122 and the bottom wall 124 and defining an outer perimeter of the inflatable balloon 120. In some embodiments, the inflatable balloon 120 may comprise a plurality of inner walls 130 each extending between the top wall 122 and the bottom wall 124. In some embodiments, the plurality of inner walls 130 may limit how far apart the top wall 122 and the bottom wall 124 may.

Turning back to FIG. 7, the inflatable balloon 120 may comprise a plurality of internal chambers 140 defined by the plurality of inner walls 130, including a central internal chamber 142. In some embodiments, the inflatable balloon 120 may comprise a series of interconnected longitudinally-oriented internal chambers 140 including a central internal chamber 142 and several laterally disposed internal chambers 144. In some embodiments, the inflatable balloon 120 may comprise five internal chambers 140, including the central internal chamber 142. Other configurations are also contemplated, including but not limited to, three chambers, four chambers, six chambers, seven chambers, etc.

Figure 7:
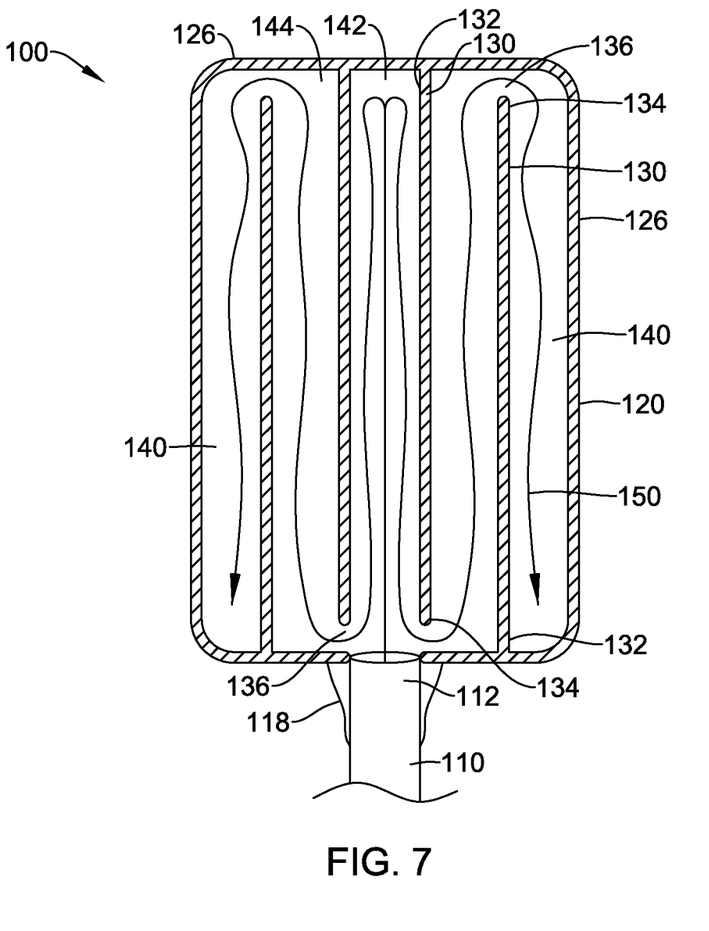
FIG. 7 is a partial section view of an example dissection device.

Each of the plurality of inner walls 130 may be in sealing contact with the outer perimeter wall 126 at a first end 132 of the inner wall 130. In some embodiments, the first end 132 of each of the plurality of inner walls 130 may be bonded to and/or integrally formed with the top wall, 122, the bottom wall 124, and/or the outer perimeter wall 126. Each of the plurality of inner walls 130 may include a second end 134 opposite the first end 132. In at least some embodiments, each of the plurality of inner walls 130 may be oriented generally parallel to a central longitudinal axis of the catheter 110. In some embodiments, a relative position of the first end 132 of each inner wall 130 within the inflatable balloon 120 and a relative position of the second end 134 of each inner wall 130 within the inflatable balloon 120 may be transposed on adjacent inner walls 130. In other words, the first end 132 and the second end 134 may alternate or "flip flop" from one inner wall 130 to a laterally adjacent inner wall 130.

In some embodiments, the second end 134 may be spaced apart from the outer perimeter wall 126 so as to form an opening 136 between adjacent chambers. In some embodiments, each laterally disposed internal chamber 144 may include an opening 136 fluidly connecting to each adjacent chamber. In other words, there may be one opening 136 between each pair of adjacent internal chambers 140. In some embodiments, the opening 136 connecting the central internal chamber 142 to each immediately adjacent laterally disposed internal chamber 144 may be disposed proximate a first end of the inflatable balloon 120. In some embodiments, the first end of the inflatable balloon 120 may be a proximal end of the inflatable balloon 120, or the first end of the inflatable balloon 120 may be a distal end of the inflatable balloon 120. In some embodiments, each opening 136 fluidly connecting the internal chambers 144 immediately adjacent to the central internal chamber 142 to an immediately adjacent, laterally outwardly disposed internal chamber 144 is positioned proximate a second opposing end of the inflatable balloon 120. The second end of the inflatable balloon 120 may be disposed longitudinally opposite the first end of the inflatable balloon 120. In some embodiments, the second end of the inflatable balloon 120 may be a distal end of the inflatable balloon 120, or the second end of the inflatable balloon 120 may be a proximal end of the inflatable balloon 120. Similar to the discussion above with respect to the first end 132 and the second end 134 of the inner walls 130, the openings 136 may alternate or "flip flop" from end to end of the inflatable balloon 120 between laterally adjacent inner walls 130.

In some embodiments, a distance between two opposing points on the outer perimeter wall 126 in a plane through a center of the inflatable balloon 120 may be greater than a distance from the top wall 122 to the bottom wall 124 measured perpendicular to the plane through the center of the inflatable balloon 120. In some embodiments, the distance from the top wall 122 to the bottom wall 124 measured perpendicular to the plane through the center of the inflatable balloon 120 may decrease in a direction laterally outward from the center of the inflatable balloon 120 within the plane through the center of the inflatable balloon 120. Other configurations, including a generally constant distance from the top wall 122 to the bottom wall 124 in the direction laterally outward from the center of the inflatable balloon 120, are also contemplated. In at least some embodiments, the central longitudinal axis of the catheter 110 lies within the plane through the center of the inflatable balloon 120.

In some embodiments, the catheter 110 may have an inflation lumen extending through the catheter 110 to an interior space defined within the inflatable balloon 120. In some embodiments, the central internal chamber 142 may be in direct, unimpeded fluid communication with the inflation lumen, as seen in FIG. 7 for example. In some embodiments, the series of interconnected longitudinally-oriented internal chambers 140 may be configured to inflate laterally outward from the central internal chamber 142. In other words, inflation media introduced into the interior space of the inflatable balloon 120 through the inflation lumen may fill the plurality of internal chambers 140 sequentially from the central internal chamber 142 outward, as indicated by an example fluid flow path 150 shown in FIG. 7. In at least some embodiments, the inflation media may be cooled to reduce and/or minimize inflammatory reaction(s) by the tissue layers of the parietal peritoneum 40 and the transversalis fascia 42 as the inflatable balloon 120 is expanded to dissect the tissue layers of the parietal peritoneum 40 and the transversalis fascia 42 and form the abdominal pouch 44.

In some embodiments, the inflation lumen extending through the catheter 110 may be in direct, unimpeded fluid communication with a first outermost chamber (e.g., a leftmost chamber or a rightmost chamber) of the plurality of internal chambers 140, and the series of interconnected longitudinally-oriented internal chambers 140 may be configured to inflate laterally in sequence from the first outermost chamber toward the central internal chamber 142 and continuing on toward the other, opposing outermost chamber. In at least some embodiments where the inflation lumen is in direct, unimpeded fluid communication with the first outermost chamber, the inflatable balloon 120 may be rolled in a single direction and/or to form a single helical shape in the collapsed delivery configuration, wherein introduction of inflation media into the inflatable balloon 120 inflates and/or unrolls the inflatable balloon 120 laterally in a single direction only. In addition to being made and/or developed as described above, such an arrangement may be seen in and/or obtained from, for example, one side and/or approximately one half of the structure and/or arrangement shown in FIGS. 4 and 5. Similarly, the operation and function of such an arrangement may also taken, as appropriate, from the earlier description of FIGS. 4 and 5.

In some embodiments, each of the plurality of internal chambers 140 may have a generally rectangular cross-section, as seen in FIG. 8 for example. As viewed in cross-section, a width of each of the plurality of internal chambers 140 may increase in each successive laterally outward internal chamber 144 from the central internal chamber 142, and a height or overall thickness of each of the plurality of internal chambers 140 may decrease in each successive laterally outward internal chamber 144 from the central internal chamber 142. In some embodiments, the central internal chamber 142 of the plurality of internal chambers 140 may have a generally circular or round cross-section, and each successive internal chamber 144 disposed laterally outward from the central internal chamber 142 may have an elliptical cross-section, as seen in FIG. 9 for example. The elliptical cross-section may have a major dimension greater than a diameter of the central internal chamber 142, and the major dimension may increase in each successively further laterally outward internal chamber 144. In other words, as viewed in cross-section, a width of each of the plurality of internal chambers 140 may increase in each successive laterally outward internal chamber 144 from the central internal chamber 142, and a height or overall thickness of each of the plurality of internal chambers 140 may decrease in each successive laterally outward internal chamber 144 from the central internal chamber 142. Generally speaking, a cross-sectional profile of the inflatable balloon 120 may be generally flattened (wider and/or longer than it is tall or thick). In other words, the inflatable balloon 120 may not have a bulbous three-dimensional shape.

In use, a method of forming an abdominal pouch 44 within an abdominal wall 20 may include inserting a dissection device 100 through an incision in the skin of a patient and between a first layer of tissue of the abdominal wall 20 and a second layer of tissue of the abdominal wall 20 immediately adjacent the first layer of tissue (e.g., the parietal peritoneum 40 and the transversalis fascia 42), the dissection device 100 including an inflatable balloon 120 disposed at a distal end of a catheter 110. The inflatable balloon 120 may comprise a top wall 122, a bottom wall 124 spaced apart from the top wall 122, an outer perimeter wall 126 extending between the top wall 122 and the bottom wall 124, and a plurality of inner walls 130 each extending between the top wall 122 and the bottom wall 124 and in sealing contact with the outer perimeter wall 126 at a first end 132 of the inner wall 130. The method may include positioning the dissection device 100 and/or the inflatable balloon 120 at a desired location or target site of the abdominal pouch 44 within the abdominal wall 20. The method may include inflating the inflatable balloon 120 within the abdominal wall 20 with an inflation media from the central internal chamber 142 laterally outward, thereby slowly separating the first layer of tissue from the second layer of tissue to form the abdominal pouch 44 within the abdominal wall 20. After forming the abdominal pouch 44 within the abdominal wall 20, the method may further include deflating the inflatable balloon 120 within the abdominal wall 20, and withdrawing the dissection device 100 and/or the inflatable balloon 120 from the abdominal wall 20. The abdominal pouch 44 may thereafter be used to accept and/or accommodate a medical implant, such as a diabetes reversing implant, a pacemaker, a defibrillator, or other suitable device. The location of the pouch between the parietal peritoneum 40 and the transversalis fascia 42 may facilitate vascularization of the area following implantation, to facilitate transfer of treatment drugs, particles, and/or other elements from the medical implant into the body and/or bloodstream, for example.

The materials that can be used for the various components of the dissection device 100, the catheter 110, the inflatable balloon 120, the outer sleeve 160, etc. (and/or other systems disclosed herein) and the various elements thereof disclosed herein may include those commonly associated with medical devices. For simplicity purposes, the following discussion makes reference to the dissection device 100, the catheter 110, the inflatable balloon 120, the outer sleeve 160, etc. However, this is not intended to limit the devices and methods described herein, as the discussion may be applied to other elements, members, components, or devices disclosed herein, such as, but not limited to, the top wall 122, the bottom wall 124, the outer perimeter wall 126, the inner walls 130, etc. and/or elements or components thereof.

In some embodiments, the dissection device 100, the catheter 110, the outer sleeve 160, etc., and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the dissection device 100, the catheter 110, the inflatable balloon 120, the outer sleeve 160, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the dissection device 100, the catheter 110, the inflatable balloon 120, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the dissection device 100, the catheter 110, the inflatable balloon 120, the outer sleeve 160, etc. to achieve the same result.

In some embodiments, a degree of Magnetic Resonance Imaging (MRI) compatibility is imparted into the dissection device 100, the catheter 110, the inflatable balloon 120, the outer sleeve 160, etc. For example, the dissection device 100, the catheter 110, the inflatable balloon 120, the outer sleeve 160, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The dissection device 100, the catheter 110, the inflatable balloon 120, the outer sleeve 160, etc., or portions thereof, may also be made from a material that the MRI machine can image. Some materials that exhibit these characteristics include, for example, tungsten, cobalt-chromium-molybdenum alloys (e.g., UM: R44003 such as ELGILOY®, PHYNOX®, and the like), nickel-cobalt-chromium-molybdenum alloys (e.g., UM: R44035 such as MP35-N® and the like), nitinol, and the like, and others.

In some embodiments, the dissection device 100, the catheter 110, the inflatable balloon 120, the outer sleeve 160, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A dissection device, comprising:
   an inflatable balloon extending distal of a distal end of a catheter, the catheter having an inflation lumen extending through the catheter to an interior space defined within the inflatable balloon, wherein the inflatable balloon comprises:
   a top wall;
   a bottom wall spaced apart from the top wall;
   an outer perimeter wall extending between the top wall and the bottom wall; and
   a plurality of inner walls each extending between the top wall and the bottom wall and in sealing contact with the outer perimeter wall at a first end of the inner wall, each of the plurality of inner walls including a second end opposite the first end, the second end being spaced apart from the outer perimeter wall, wherein a relative position of the first end of each inner wall within the inflatable balloon and a relative position of the second end of each inner wall within the inflatable balloon are transposed on adjacent inner walls.

2. The dissection device of claim 1, wherein a distance between two opposing points on the outer perimeter wall in a plane through a center of the inflatable balloon is greater than a distance from the top wall to the bottom wall measured perpendicular to the plane through the center of the inflatable balloon.

3. The dissection device of claim 2, wherein the distance from the top wall to the bottom wall measured perpendicular to the plane through the center of the inflatable balloon decreases in a direction laterally outward from the center of the inflatable balloon within the plane.

4. The dissection device of claim 2, wherein a central longitudinal axis of the catheter lies within the plane through the center of the inflatable balloon.

5. The dissection device of claim 1, wherein the inflatable balloon comprises a plurality of internal chambers defined by the plurality of inner walls.

6. The dissection device of claim 5, wherein the inflation lumen is fluidly connected directly to a central internal chamber of the plurality of internal chambers.

7. The dissection device of claim 6, wherein inflation media introduced into the interior space through the inflation lumen fills the plurality of internal chambers sequentially from the central internal chamber outward.

8. The dissection device of claim 6, wherein the central internal chamber includes a generally circular cross-section.

9. The dissection device of claim 8, wherein each internal chamber disposed laterally outward from the central internal chamber has an elliptical cross-section.

10. The dissection device of claim 9, wherein the elliptical cross-section has a major dimension greater than a diameter of the central internal chamber.

11. The dissection device of claim 10, wherein the major dimension increases in each successively further outward internal chamber.

12. The dissection device of claim 1, wherein each of the plurality of inner walls are oriented generally parallel to a central longitudinal axis of the catheter.

13. The dissection device of claim 1, wherein a proximal end of the inflatable balloon includes a proximally tapered portion coupled to an outer surface of the catheter.

14. A dissection device for forming a pouch in an abdominal wall, comprising:
   a catheter extending along a longitudinal axis and having an inflation lumen extending longitudinally therethrough; and
   a non-compliant inflatable balloon extending distally from a distalmost end of the catheter in fluid communication with the inflation lumen, the inflatable balloon being expandable from a collapsed delivery configuration to an expanded configuration having a generally flattened profile;
   wherein the inflatable balloon comprises a series of interconnected chambers oriented parallel to the longitudinal axis and including a central chamber in direct fluid communication with the inflation lumen, and laterally disposed chambers each having an opening fluidly connecting to each adjacent chamber;
   wherein the series of interconnected longitudinally-oriented chambers is configured such that the central chamber is inflated first and adjacent chambers are inflated sequentially and laterally outward from the central chamber.

15. The dissection device of claim 14, wherein the inflatable balloon includes a proximally tapered portion coupled to an outer surface of the catheter.

16. The dissection device of claim 14, wherein the opening fluidly connecting the central chamber to each immediately adjacent chamber is positioned proximate a first end of the inflatable balloon.

17. The dissection device of claim 16, wherein each opening fluidly connecting the chambers immediately adjacent to the central chamber to an immediately adjacent, laterally outwardly disposed chamber is positioned proximate a second opposing end of the inflatable balloon.

18. A method of forming a pouch within an abdominal wall, comprising:

inserting a dissection device between a first layer of tissue of the abdominal wall and a second layer of tissue of the abdominal wall immediately adjacent the first layer of tissue, the dissection device including an inflatable balloon extending distal of a distalmost end of a catheter extending along a longitudinal axis, the catheter including an inflation lumen, the inflatable balloon comprising:
  a series of interconnected chambers oriented parallel to the longitudinal axis and including a central chamber in direct fluid communication with the inflation lumen, and laterally disposed chambers each having an opening fluidly connecting to each adjacent chamber, the series of interconnected longitudinally-oriented chambers being configured such that the central chamber is inflated first and adjacent chambers are inflated sequentially and laterally outward from the central chamber;
positioning the inflatable balloon of the dissection device at a desired location of the pouch within the abdominal wall;
sequentially inflating the chambers of the inflatable balloon from the central chamber and laterally outward within the abdominal wall, thereby separating the first layer of tissue from the second layer of tissue to form the pouch within the abdominal wall;
deflating the inflatable balloon within the abdominal wall; and
withdrawing the dissection device from the abdominal wall.

* * * * *